United States Patent [19]

O'Young et al.

[11] Patent Number: 5,510,560

[45] Date of Patent: * Apr. 23, 1996

[54] SKELETAL ISOMERIZATION OF N-OLEFINS TO ISO-OLEFINS ON BINDED FERRIERITE ZEOLITES

[75] Inventors: Chi–Lin O'Young, Poughkeepsie; Regis J. Pellet, Croton-On-Hudson; Alison E. Hadowanetz, Maybrook; John Hazen, Cragsmoor; James E. Browne, Beacon, all of N.Y.

[73] Assignee: Texaco Inc., White Plains, N.Y.

[*] Notice: The portion of the term of this patent subsequent to Feb. 13, 2003, has been disclaimed.

[21] Appl. No.: 112,921

[22] Filed: Aug. 30, 1993

[51] Int. Cl.$^6$ ................................ C07C 5/22; C07C 5/27
[52] U.S. Cl. ................................................ 585/671
[58] Field of Search ............................................ 585/671

[56] References Cited

U.S. PATENT DOCUMENTS 3,965,209  6/1976  Butter et al. ........................ 585/454
5,157,194  10/1992  Rahmin et al. ...................... 585/671
5,321,194  6/1994  Apelian et al. ...................... 585/671

Primary Examiner—E. Rollins Cross
Assistant Examiner—E. D. Irzinski

[57] ABSTRACT

The method of converting n-butylenes to isobutylene by a skeletal isomrization reaction wherein said reaction is carried out at a temperature of between 300° C. and 650° C., under a pressure of between 0.1 and 100 atmospheres and a space velocity of said n-butylenes of between 0.1 and 40 WHSV using a cagalyst comprising a zeolite binder selected frm the group consisting of alumina, silica, silica-alumina, clay and a combination thereof, said catalyst having a pore size of at least about 4.5 angstroms and the pore size structure is characteried by intersecting 10-member ring and 8-member ring channels.

7 Claims, 2 Drawing Sheets

SKELETAL ISOMERIZATION OF N-OLEFINS TO ISO-OLEFINS ON BINDED FERRIERITE ZEOLITES

BACKGROUND OF THE INVENTION

This invention relates to olefin isomerization. In one of its more specific aspects, this invention relates to selective isomerization of olefins using binder ferrierite zeolites and the synergistic effects of binders on zeolite catalysts used in such isomerization.

More particularly, the present invention relates to a process for the preparation of useful hydrocarbons by binder catalytic conversion of n-olefins.

MTBE (methyl tertiary butyl ether) is an effective octane booster. It is made from isobutylene and methanol. The present sources of isobutylene for MTBE production are mainly from by-products of steam, catalytic crackers, and propylene oxide production. However, these supplies are limited. Other possible sources are by isomerization of n-butenes taken from steam or catalytic crackers and by dehydrogenation of isobutane taken from field butanes or produced by isomerization of n-butane.

Olefin isomerization processes can be directed towards either skeletal isomerization or double bond isomerization. Skeletal isomerization is concerned with reorientation of the molecular structure in respect to the formation or elimination of side chains. Double bond isomerization is concerned with relocation of the double bond between carbon atoms while maintaining the backbone of the carbon structure. Most isomerization processes give rise only to double bond isomerization.

The minimum Brönsted Acid strengths (and equivalents in $H_2SO_4$) required for various acid-catalyzed conversions of hydrocarbons are indicated in the table below.

| Minimum Brönsted Acid Strength Required For The Acid-Catalyzed Conversions of Hydrocarbons | |
|---|---|
| $H_R$ Required | Reaction Type |
| <+0.8 1.2 wt % $H_2SO_4$ | Cis-trans Isomerization of Olefins |
| <−6.6 48 wt % $H_2SO_4$ | Double-bond Migration |
| <−11.6 68 wt % $H_2SO_4$ | Skeletal Isomerization |
| <−16.0 88 wt % $H_2SO_4$ | Cracking of Alkanes |

It is frequently necessary to convert olefins into other olefins having a different skeletal arrangement. For example, normal butenes are converted into isobutene for polymerization, alkylation, disproportionation or for the production of MTBE. Similarly, normal amylenes must be converted to isoamylenes prior to dehydrogenation to isoprene.

While a number of catalytic materials possess some activity for such a conversion, not all possess sufficient selectivity to be economical. Because the feeds are generally the relatively reactive olefins, many catalysts cause undesirable side reactions such as polymerization or cracking. Consequently, there is a continuing interest in the development of new skeletal isomerization catalysts and processes for isomerizing alkenes to improve efficiencies and to give optimum results for various industrial requirements. A comprehensive review is provided by V. R. Choudhary in "Catalytic Isomerization of n-butene to Isobutene," *Chem. Ind.* Dev, pp. 32–4 (1974).

It is generally known that n-paraffins with, for example, 4 to 7 carbon atoms can be converted to the corresponding isomeric paraffins by using suitable acid catalysts in the temperature range of from 100° to 250° C. Examples of this process are the numerous isomerization processes used in the petrochemical and mineral oil industries for increasing the octane number of light, paraffinic mineral oil fractions. Furthermore, it is known that, in contrast to this, olefins of the same number of carbon atoms cannot be converted to the corresponding isoolefins except under difficult conditions, for example at very high temperatures and with poor yield. The attempts hitherto described in the literature for the direct isomerization of the skeleton of e.g. n-butene to give isobutene or e.g. of n-pentene to give isopentenes over catalysts arranged in a fixed bed are characterized by initially relatively low yields and selectivities, which diminish and deteriorate further after a short period of operation, often after only a few hours. The deterioration in the yields and selectivities is generally attributed to the loss of actively effective catalyst surface or to the loss of active centers. In addition to this, high coking rates, formation of oligomers and cracking reactions are observed.

As is known, olefins exist in various isomer. for example, butylenes or butenes exist in four isomers: butene-1, cis-butene-2, its stereo-isomer trans-butene-2, and isobutene; and pentenes exist in six isomers. Conversions between the butenes-2 are known as geometric isomerization, whereas those between butene-1 and the butenes-2 are known variously as position isomerization, double-bond migration, or hydrogen-shift isomerization. These three isomers are not branched and are known collectively as normal or n-butenes. Conversion of the n-butenes to isobutene, which is a branched isomer, is widely known as skeletal isomerization.

Similar, conversions between the 2-pentenes are known as geometric isomeration, whereas those between 1-pentene and the 2-pentenes are known variously as position isomerization, double-bond migration, or hydro-shift isomerization.

Olefins, such as isoamylenes or isobutene have become more and more important recently as one of the main raw materials used in the production of methyl tert-butyl ether (MTBE), an environmentally-approved octane booster to which more and more refiners are turning as metallic additives are phased out of gasoline production. However, processes for the skeletal isomerization of olefins e.g., to produce isobutene, are relatively non-selective, inefficient, and short-lived because of the unsaturated nature of these compounds. On the other hand, positional and skeletal isomerization of paraffins and alkyl aromatics are fairly well established processes, in general utilizing catalysts typically comprising metallic components and acidic components, under substantial hydrogen pressure. Since paraffins and aromatics are stable compounds, these processes are quite successful. The heavier the compounds, in fact, the less severe the operating requirements. Olefins, however, are relatively unstable compounds. Under hydrogen pressure, they are readily saturated to the paraffinic state if a metal component is present in the catalyst.

Furthermore, in the presence of acidity, olefins can polymerize, crack and/or transfer hydrogen. Extensive polymerization would result in poor yields, and short operating cycles. Similarly, cracking would reduce yield. Hydrogen transfer would result in saturated and highly unsaturated compounds, the latter being the common precursors for gum and coke. Any theoretical one step process for producing skeletal isomers of, for example, n-butenes or amylenes, would have to be concerned with the unwanted production of olefin oligomers and cracked products. In addition to these problems, it is well known that skeletal isomerization becomes more difficult as hydrocarbons get lighter.

Skeletal isomerization of olefins is known to be accomplished by contacting unbranched or lightly branched olefins with acidic catalysts at elevated temperatures. The process is generally applicable to the isomerization of olefins having from 4 to about 20 carbon atoms and is especially applicable to olefins having from 4 to about 10 carbon atoms per molecule. The process may be used to form isobutene from normal butylenes, methyl pentenes and dimethyl butenes from normal hexenes, and so forth.

In making the isomerization of these olefins, the zeolite crystallites, i.e., catalysts, are usually bound together within a matrix or binder generally comprised of alumina, silica, silica-alumina, clay or admixtures thereof to enhance the performance of the zeolite catalysts (e.g., the yield of product).

Thus, among the objects of this invention are improved processes for the skeletal isomerization of n-butylene and olefins, especially for the isomerization of n-butylene to form isobutylene with zeolite catalysts to enhance the performance bound of the catalysts.

Other objects and advantages of the invention will be apparent from the following description, including the drawing and the appended claims.

DISCLOSURE STATEMENT

Known skeletal isomerization catalysts include aluminas and halogenated aluminas, particularly F- or Cl-promoted aluminas. Supports employed in such catalysts are either alumina or predominantly alumina due mainly to the high acidity of alumina. See Choudhary, V. R., "Fluorine Promoted Catalysts: Activity and Surface Properties", *Ind. Eng. Chem., Prod. Res. Dev.*, 16(1), pp. 12–22 (1977) and U.S. Pat. No. 4,400,574. Numerous catalysts employ a metal or metal oxide in conjunction with a halide-treated metal oxide. For example, U.S. Pat. No. 4,410,753 discloses isomerization catalysts comprising $Bi_2O_3$ on fluorided alumina and U.S. Pat. No. 4,433,191 discloses skeletal isomerization catalysts comprising a Group VIII metal on halided alumina. Many of the catalysts including halide-treated components require periodic addition of halide materials to maintain catalyst activity; for example, see U.S. Pat. Nos. 3,558,734 and 3,730,958. An average yield for isobutene of 25 weight percent (within an observed range of 17 to 33 percent) is typically reported when using halided catalysts, based upon a review of various patents cited in this disclosure.

Various techniques have been employed to improve the effectiveness of materials such as alumina and silica as structural isomerization catalysts. For example, U.S. Pat. No. 3,558,733 discloses methods for activating alumina catalysts with steam, U.S. Pat. No. 4, 405,500 discloses catalysts prepared by controlled deposition of silica on alumina and U.S. Pat. No. 4,587,375 discloses a steam-activated silicalite catalyst. In addition, various metal oxides have been used to improve the effectiveness of catalysts based upon alumina, silica or the like.

Zeolitic materials, especially in their hydrogen forms, are known to behave as strong acids. Due to their narrow yet regular pore size they are quite effective in catalyzing olefin polymerization. Unfortunately the pores are soon plugged due to deposition of polymeric materials and frequent catalyst regeneration is necessary to maintain activity.

U.S. Pat. No. 4,503,292, assigned to Standard Oil Co. (Indiana), discloses processes for converting n-alkenes to isoalkenes using catalysts containing AMS-1B borosilicate as at least 50 weight percent of the catalyst composition. The borosilicate can be cation-exchanged with hydrogen or metals selected from Groups IB, IIA, IIB, IIIA, VIB and VIII as well as manganese, vanadium, chromium, uranium and rare earth elements. The borosilicate can also be impregnated with metals of Groups IB, IIA, IIB, IIIA, IVB, VB, VIB, VIIB and VIII and rare earth elements.

U.S. Pat. No. 4,435,311, also assigned to Standard Oil Co. (Indiana) discloses a process for regenerating catalysts containing AMS-1B borosilicates and noble metals by contacting them with water. The process can be carried out during the process of conversion of feedstocks such as alkanes and alkenes to isomerized products such as isoolefins. Similar conversion processes employing catalysts containing such borosilicates are disclosed in U.S. Pat. Nos. 4,777,310; 4,503,282; 4,499,325 and 4,499,326, all assigned to Standard Oil or Amoco Corp.

Copending U.S. patent application, Ser. No. 07/738,016 discloses normal olefins such as n-butenes can be converted to branched olefin species such as isobutylene by skeletal isomerization over catalysts of borosilicate zeolites having pore sizes of at least about 5 Angstroms and containing boron in the framework structure thereof. The borosilicates have sufficient acidity to catalyze the skeletal isomerization of normal olefins. The catalysts can be used to produce isoolefins for reaction with alcohols in integrated processes to produce alkyl tertiary alkyl ethers such as MTBE.

Copending U.S. application, Ser. No. 07/990,407 discloses the conversion of normal olefins such as n-butylenes can be converted to branched olefin species such as isobutylene by skeletal isomerization over zeolite-based catalysts having pore sizes of at least about 4.5 Angstroms and a pore structure characterized by intersecting 10-MR and 8 MR channels. The zeolite-based catalysts have sufficient acidity to catalyze the skeletal isomerization of normal olefins. the catalysts can be used to produce isoolefins for reaction with alcohols in integrated processes to produce alkyl tertiary alkyl ethers such as MTBE.

Copending U.S. application, Ser. No. 07/990,562 discloses the conversion of normal olefins such as n-pentebes cab be converted to branched olefin species such as isopentenes by skeletal isomerization over zeolite-based catalysts having pore sizes of at least about 4.5 Angstroms and a pore structure characterized by intersecting 10-MR and 8 MR channels. The zeolite-based catalysts have sufficient acidity to catalyze the skeletal isomerization of normal olefins. The catalysts can be used to produce isoolefins for reaction with alcohols in integrated processes to produce tertiary amyl methyl ethers such as TAME.

The disclosures in the foregoing U.S. patent applications relating to the conversion of normal olefins, namely U.S. patent applications, Ser. Nos. 07/990,407 and 07/990,562 are incorporated herein in their entirety by reference.

SUMMARY OF THE INVENTION

In accordance with the present invention, a catalyst composition for the skeletal isomerization of normal olefins comprises at least one zeolite catalyst. A binder of an inorganic oxide such as alumina, silica, silica-alumina, clays and combinations thereof can optionally be employed with the zeolite based catalyst to enhance its effectiveness in the isomerization of olefins.

The zeolite based catalyst can be naturally occurring or prepared by a process comprising the steps of:

(a) preparing a basic reaction mixture of at least about pH 9 comprising in suitable proportions a silicon source, an alumina source, an organic template, and optionally, an alkali metal;

(b) heating the reaction mixture in a closed vessel under conditions of temperature, autogenous pressure and time effective to produce a crystalline product containing oxides of said zeolite based catalyst in the framework structure thereof;

(c) recovering the crystalline product; and (d) calcining the crystalline product under conditions effective to remove the organic template without substantial damage to the framework structure of the crystalline product.

To achieve the calcining effect which removes the organic template if present without damaging the crystal structure, the product is preferably subjected to at least one period of calcining in an inert atmosphere such as nitrogen, followed by at least one period of calcining in an atmosphere containing oxygen. The zeolite based catalysts can be converted to the hydrogen form by cation-exchanging with ammonium ion to remove sodium, then calcining to remove ammonia. The exchange step can be eliminated if certain organic templates containing tetraalkyl ammonium ions are used, as calcining drives off ammonia and organic residues, with hydrogen ions remaining.

A method of converting n-butylenes to isobutylene by a skeletal isomerization reaction wherein said reaction is carried out at a temperature of between 300° C. and 650° C., a pressure of said n-butylenes of between 0.1 and 100 atmospheres and a space velocity of said n-butylenes of between 0.1 and 40 WHSV using a catalyst comprising a zeolite binder selected from the group consisting of alumina, silica, silica-alumina, clay and a combination thereof, said catalyst.

Isomerization conditions include temperatures in the range of about 300° to 650° C., preferably about 400° C. to 580° C. pressures ranging from about 0.1 to about 100 atmosphere and weight hourly space velocities (WHSV) ranging from about 0.1 to about 40 weight of n-olefin/weight of catalyst per hour. The normal olefins can have from 4 to about 12 carbon atoms, preferably about 4 to 6, and preferably include n-butene.

In a preferred embodiment, the normal olefins are contained in a feedstock which may also contain branched olefins, and the product of the skeletal isomerization step is reacted with an alkanol having from 1 to about 5 carbon atoms (such as methanol or ethanol) under catalytic conditions effective to produce at least one methyl tertiary-alkyl ether, such as methyl tertiary-butyl ether, or ethyl tertiary-butyl ether.

DETAILED DESCRIPTION OF THE INVENTION

Figure 1:
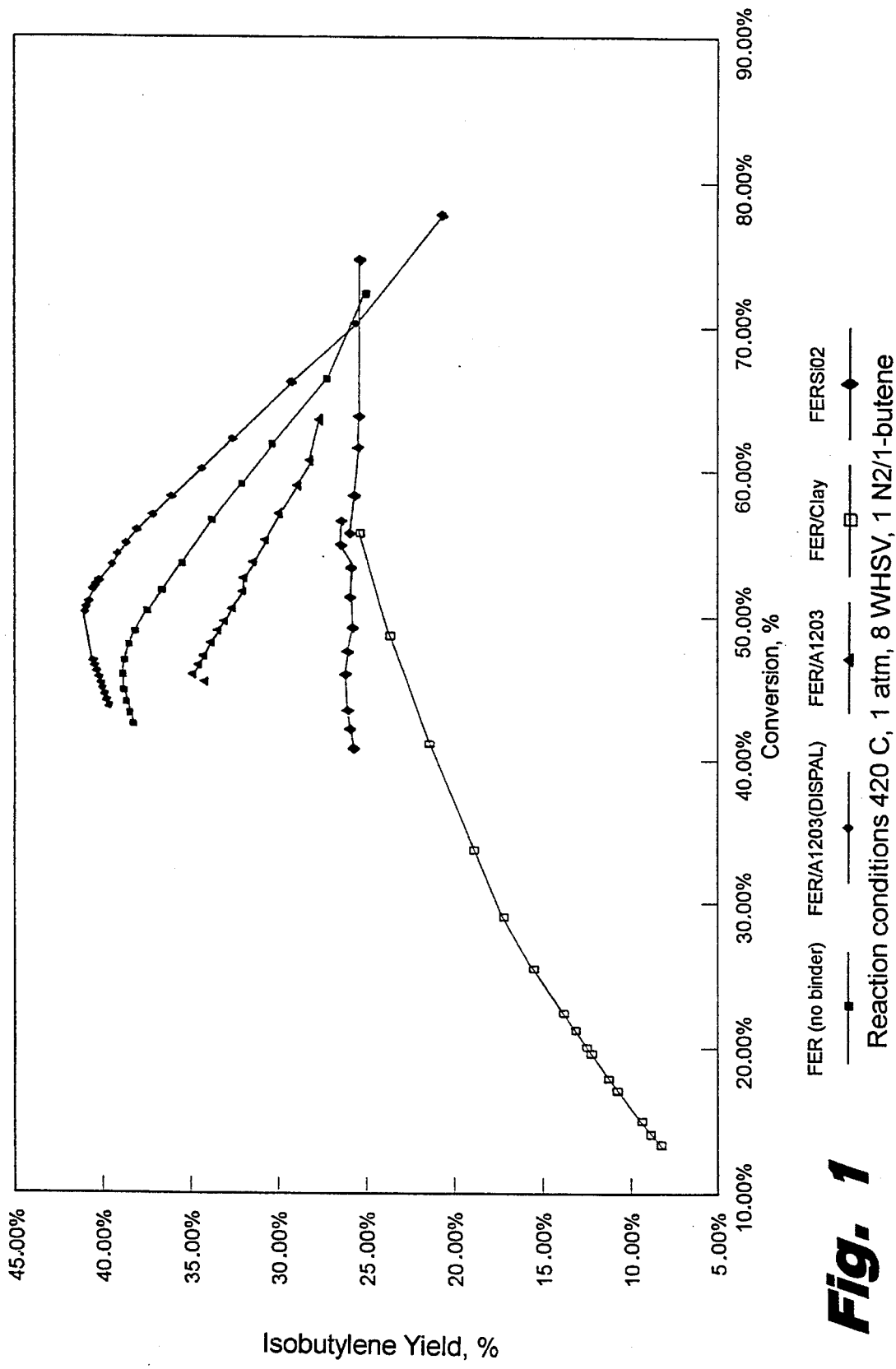
FIG. 1 is a graph of plots of isobutylene yield vs. conversion of ferrierite catalysts with different binders.

Because of their unique pore structures, zeolites exhibit the so-called shape selectivity. In the isomerization of n-butenes to isobutylene, the oligomerization is the major competitive reaction. It has been postulated that a larger space is favorable for the oligomerization reaction because two olefin molecules are involved, therefore the oligomerization will be suppressed in a smaller pore structure.[1] J. M. Thomas has predicted that Theta-1 is better than ZSM-5 for the isomerization of n-butene. Both zeolites have 10-member ring channels and pore sizes 4.5 to 5.0 A. In ZSM-5 the channels intersect, creating bigger cavities. However, in Theta-1, the channels do not intersect, and there are no extra cavities.

[1] J. M. Thomas, Scientific American, PP 112–118, April, 1992.

For the purpose of this application, a medium pore zeolite is one with a channel of 10 member ring (10-MR) and a size greater than 4.5 A. The preferred structures are those with 10-MR and 8-member ring (8-MR) intersecting channels, such as ferrierite. In Table I, below, there is a list of zeolites useful according to the present invention.

[1] J. M. Thomas, Scientific American, PP 112–118, April, 1992.

TABLE I

ZEOLITES WITH 10 AND 8-MR INTERSECTED CHANNELS

| NAME | CHANNELS | ISOTOPIC FRAMEWORK STRUCTURES |
|---|---|---|
| Dachiardite(DAC) | [010] 10 3.4 × 5.3*<–> | |
| | [001] 8 3.7 × 4.8* | |
| Epistilbite(EPI) | [100] 10 3.4 × 5.6*<–> | |
| | [001] 8 3.7 × 5.2* | |
| Ferrierite(FER) | [001] 10 4.2 × 5.4* | ZSM-35, NU-23, |
| | [010] 8 3.5 × 4.8* | FU-9, ISI-6 |
| Heulandite(HEU) | [100] 8 2.6 × 4.7*<–> | |
| | [001] 10 3.0 × 7.6*+ | |
| Stilbite(STI) | [100] 10 4.9 × 6.1<–> | |
| | [101] 8 2.7 × 5.6* | |

<–>interconnecting channels
1. Data obtained from "Atlas of Zeolite Structure Types," by W. M. Meier and D. H. Olson, Butterworths, 1987, 2nd Edition.

When the zeolites are prepared in the presence of organic cations they are initially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of the zeolite but these cations favor the formation of the desired crystal structures.

In commercial practice, the zeolite crystallites would be bound together within a matrix comprising alumina, silica-alumina, clay or admixtures thereof. Normally, the finished catalyst would contain at least 10 up to about 85 weight percent of such a binder or matrix. The alumina which is used for the matrix material for the catalyst system of the present invention can be any suitable grade of crystalline or amorphous alumina which is substantially inert.

Alumina, silica, and clay are common binders used in the manufacture of zeolite catalysts to provide mechanical strength to form catalyst particles. The binder is usually assumed to be essentially an inert component of the catalysts. However, the binder could affect the catalyst performance to some extent because of its inherent acidity or the transformation of Si and Al from the zeolite framework. Therefore, it is desirable to have a binder that not only provide the mechanical strength, but also improve the yield and catalyst stability.

In copending U.S. patent applications, Ser. Nos. 07/990, 407 and 07/990,562, ferrierite catalysts has been used for the isomerization n-olefins to iso-olefins. However, in the present invention, binders are used which provide the mechanical strength and also show synergistic effects to improve the iso-olefin yield and catalyst stability.

Silica-alumina materials which can be used as binders can be prepared in the same manner as amorphous silica-alumina catalysts, e.g., by adding the zeolite component to a silica-alumina slurry, spray drying, washing the product and drying. Optionally, a clay diluent can be present in the silica-alumina slurry. Such matrixes can be prepared by admixing colloidal alumina (boehmite) and colloidal silica, allowing the matrix properties to vary over a wide range from catalytically inert to active. The activity, thermal stability, surface area and pore distribution of the matrix can be controlled by varying the amounts and particle size distributions of the respective colloids. Further guidance for the preparation of zeolite catalysts containing high porosity matrixes such as silica-alumina can be found in the section by Magee and Blazek on "Zeolite Cracking Catalysts" in ACS Monograph 171, *Zeolite Chemistry and Catalysts* (J. Rabo, Ed.; Am. Chem. Soc., Wash, D.C. 1976).

The zeolite can also be composited with a porous clay matrix material which has suitable binding properties and is resistant to the temperature and other conditions employed in the process. The composite is then calcined to confer the required physical strength. Naturally occurring clays can be composited with the zeolite and these clays can be used in the raw state as originally mined or initially subjected to calcination, acid treatment, chemical modification or purification.

Examples of suitable clays which can be used include the bentonite and kaolin families. Bentonites are mixtures of clays, mainly montmorillonites, which may also contain kaolinite clays. The Wyoming bentonites and montmorillonites are preferred because of their relatively high purity. Kaolin clays include, for example, the Dixie, McNamee-Georgia and Florida clays and others in which the main mineral constituent is halloysite, kaolinite, dickite, nacrite or anauxite. Other clays may also be found to be suitable for use in the present process.

The amount of clay or other matrix material relative to zeolite in the composite will determine, to a certain extent, the physical strength of the final catalyst, especially its attrition resistance and crushing strength. The mechanical properties of the catalyst can therefore be modified by appropriate choice of matrix/zeolite ratio, with greater amounts of matrix generally conferring better mechanical properties. On the other hand, larger amounts of matrix mean that less of the zeolite with its desired, attendant properties will be available to participate in the eventual reaction. A balance will therefore be struck, in most cases, between activity and mechanical properties. Normally, the amount of matrix material will not exceed 50 percent by weight of the composite and in most cases it will not exceed 40 percent by weight and may be lower, e.g. 25 percent by weight or even 15 percent by weight.

The zeolite may conveniently be composited with the clay or other matrix materials by forming an aqueous slurry of the zeolite with the matrix material, spray drying the slurry to form micro-spheres and then calcining. Alternatively, extrudates, pellets and beads can be formed from matrix and zeolite mixtures. If one of the zeolites in the zeolite combination is capable of being produced by treatment of a clay, the zeolite may be composited with the clay slurry and the slurry spray dried to form solid zeolite/clay microspheres which are then calcined to confer the desired strength. The clay in the composite may then be converted to the zeolite in the conventional way, e.g. by treatment with sodium hydroxide and heating, followed by ion-exchange, if desired. The mixing and homogenizing steps which may be used in the preparation of the zeolite-matrix mixtures are conventional and need not be described; the spray drying may also be carried out in the conventional manner.

Spent catalysts can be regenerated by heating in a similar oxygen-containing gas, such as air, at temperatures ranging from about 200° C. to about 700° C. This process is significantly simpler than that required for halided metal oxide catalysts, in which a separate step of replacing the halide component must be employed.

The skeletal isomerization processes of this invention are carried out by contacting the feed with the catalyst, using any suitable contacting techniques, at temperatures at which skeletal isomerization of the feed of olefins occurs. The feed is preferably maintained in the vapor phase during contacting. The reactor temperature is preferably in the range of about 300° to about 650° C., more preferably about 400° to about 580° C. The weight hourly space velocity (WHSV) is not narrowly critical but will generally be within the range of about 0.1 to about 40 $hr^{-1}$, preferably from about 1 to about 20 $hr^{-1}$. Any convenient pressure can be used, with the lowest practical pressure preferred in order to minimize side reactions such as polymerization. Preferred pressures are within the range of about 0.1 to about 10 atmospheres, more preferably about 1 to about 4 atmospheres.

The isomerization feedstock contains at least one alkene. Alkenes having 7 or more carbon atoms are generally more likely to crack into light gases than to undergo skeletal isomerization. The alkenes may have terminal or internal double bonds. Butene feedstocks may contain 1-butene, 2-butene or mixtures thereof. Examples of other normal alkenes which are useful feedstocks are 1- and 2-pentenes; 1-, 2- and 3-hexenes; 1-, 2-, and 3-heptenes; and 1-, 2-, 3-, and 4-octenes.

Particular feedstocks contemplated for use in the present process are fractions containing butenes, e.g., n-butenes. Isobutene present in such fractions is commonly converted by catalytic reaction with methanol to produce methyl tertiary-butyl ether ("MTBE"). MTBE is separated by distillation, leaving a residual ($C_4$) cut. Isobutene present in such fractions may also be oligomerized to produce oligomers which are then separated, again leaving a residual $C_4$ cut. In either MTBE production or oligomerization, a mixture of n-butenes and isobutene remains in,the residual material. It is desirable to produce additional isobutene from the residual material and return the isobutene for further conversion by the reactions mentioned above.

The isomerization feed stream can contain inert gaseous diluents (e.g. paraffins, $N_2$, steam, etc.). The diluent may be present in any desired proportion, e.g., up to about 80 weight percent of the feed stream. Hydrogen can be present in the feed stream in addition to such diluents, and with or without steam can have beneficial effects on the product yield and selectivity.

Selection of isomerization conditions is dependent on the olefins to be isomerized. In general, lower temperatures are used for feeds containing larger olefin molecules. Depending on the specific skeletal isomerization catalysts chosen to carry out the steps of the invention, any suitable reaction technique can be utilized, such as fixed bed reaction, fluidized bed reaction, liquid phase batch and continuous operations, and the like. Conventional methods can be used to separate the materials present in the reaction effluent, including fractionation, crystallization, adsorption, and the like.

Fractionation is generally preferred. Saturated materials which accumulate in the system can easily be removed by suitable techniques well known in the art.

In one aspect of the process according to the present invention, the conversion of n-alkenes into isoalkenes, preferably butylenes into isobutylene, almost up to the establishment of thermodynamic equilibrium is achieved. This equilibrium, between 400° to 500° C., is about 36 to 40 percent by weight in the case in which the pure system of the n-butylenes and isobutylene is considered. This equilibrium may not be achieved in the case of a single contact of the mixture to be employed according to the present invention with the catalyst to be employed during the present process. However, in a particular variant of the process, the product stream leaving the catalyst bed can be divided up, and only one part is directly conveyed to the working-up process, while the other part is again conducted over the catalyst bed. This division of the product stream for recycling can vary within wide limits, for example between the proportions of 1:9 to 9:1 of worked-up or recycled material. In this process, a high recycling rate implies a smaller throughput, relative to a constant catalyst charge and constant remaining reaction conditions, but brings a desired shift of the spectrum of components in favor of the isoalkene, e.g. of the isobutene, almost to the thermodynamic equilibrium. On the other hand, a lower recycling rate implies a higher throughput but a poorer approach to the thermodynamic equilibrium. A decision concerning the amount of the recycling rate depends, other process parameters being constant, above all on the composition of the starting hydrocarbon mixture which is available. However, with the catalysts according to the present invention, the process can, in general, be operated without a high recycling rate. This can be optimized by simple preliminary experiments.

The process also can be carried out under the following conditions:

1. The reactor temperature is between 300° and 650° C., the pressure is between 0.1 and 100 atmospheres, and the space velocity of n-butenes (WHSV) is between 0.1 and 40. The preferable reactor conditions are 400° to 580° C., 0.5 to 4 atm. and 1 to 20 WHSV of n-butenes.
2. Diluents, such as steam, nitrogen, etc., can be used in the feed to improve the selectivity and yield.
3. The feeds can be 1-butene, mixed n-butenes, and $C_4$-raffinates depleted in isobutylene. The process also can be applied to the other n-olefins, such as n-pentenes and n-hexenes.

According to the present invention, a preferred embodiment of the invention is directed to an integrated process for skeletal isomerization of normal butenes to produce isobutene, which is then used in the production of methyl tertiary-butyl ether (MTBE). Streams of a mixed butene feedstock and methanol are reacted in a MTBE synthesis reactor, the methanol reacting with the isobutene in the mixed feedstock to form MTBE which is then taken off via an exit line. The MTBE synthesis reactor acts as a $C_4$ separation unit, since the methanol reacts selectively with isobutene. Other mixed olefin streams could be treated in the same manner, e.g. reacting methanol with isoamylenes to form tertiary-amyl methyl ether (TAME). Other alcohol streams could be employed in a similar manner; e.g., reacting ethanol with mixed butenes to form ethyl tertiary-butyl ether (ETBE). The alcohol stream can contain at least one alkanol having from 1 to about 5 carbon atoms. Depending upon whether streams containing substantially single alcohols or mixtures thereof are employed, the corresponding alkyl tertiary-alkyl ether or mixtures containing various groups can be produced.

The product raffinate stream is fed to a skeletal isomerization unit wherein a catalyst of the present invention is employed to isomerize normal butenes and/or butanes to isobutene for recycle to the MTSE reactor via recycle line. Hydrogen or steam can be introduced into isomerization section to improve reactor performance. Saturated species which are unsuitable for isomerization can be separated and purged from the raffinate via an exit line, or as part of the by-products ($C_1$–$C_3$ gases and polygas) which are separated from the isomerization section via other exit lines.

Such an integrated process permits a mixed feed stream of butenes (or other alkanes and/or alkenes) to be used most effectively in the production of MTBE (or other alkyl tertiary-alkyl ethers) via the skeletal isomerization of alkenes and recycle to the MTBE reactor. The skeletal isomerization processes and catalysts of the present invention are of course useful in processing feed streams containing normal alkenes from a variety of sources.

EXAMPLES

The present invention is further illustrated by reference to the following Examples.

EXAMPLE I

Preparation of Catalysts

A commercially available ferrierite catalyst, TSZ-720*, was used; the catalyst contained 80% ferrierite and 20% alumina binder. The chemical composition of ferrierite had 84.7% $SiO_2$, 8.1% $Al_2O_3$, 1.45% $Na_2O$, and 5.6% $K_2O$; it was in form of [$K^+/Na^+$]. The catalyst was ion-exchanged twice with $NH_4NO_3$ to form [$NH_4^+$]-ferrierite. About 5 grams of catalyst was mixed with 20 grams of $NH_4NO_3$ and 200 milliliters of water; the mixture was stirred at 90° C. for two hours. The exchanged catalyst was washed, dried, and calcined at 600° C. to form [$H^+$]-ferrierite. The composition of the finished catalyst had 0.12% K and <0.05% Na.

*TSZ-720—Trademark of a zeolite-based ferrierite catalyst with 20% alumina binder, manufactured and sold by TOYO SODA USA, Inc. of Atlantic, Ga.

The catalysts also could be prepared by the following ways:

1. The zeolites should have a pore size bigger than the kinetic diameter of butenes, 4.5–5.0A. The favorable zeolites are those with 10-member ring (MR) and 8-MR intersecting channels. In Table I, is a list of 10-MR zeolites which can be used.
2. The zeolites can be alumina silicates and isomorphous substitution [T]-zeolites in which T is B, Ga or Fe.
3. The mole ratio of Si/Al or Si/T is between about 4 and about 1000.
4. The zeolites are in H form.
5. The pore structure of zeolites can be modified by known methods, such as steam calcination, acid wash, impregnation, ion-exchange or combination of them to enhance the shape selectivity.
6. Catalysts can be prepared with a binder, such as alumina, silica, silica-alumina, clay or a combination of them. The weight percent of the binder is between 0–99%; and the preferred binder, alumina, has size ranging from about 0.4 to about 100.0 microns.

EXAMPLE 2

Preparation of FERRRIERITE Catalyst

A Ferrierite (FER) powder, HSZ-720KOA (manufactured and sold by TOYO SODA USA, Inc. of Atlanta, Ga.) was used; the zeolite had 84.7% $SiO_2$, 8.16% $Al_2O_3$, 1.5% $Na_2O$, and 5.6% $K_2O$ in dry basis. The mole ratio of $SiO_2/Al_2O_3$ was 17.6. About 1000 g of FER powder was mixed with 1000 g of $NH_4NO_3$ and 2500 g of water at 90° C. with stirring for 2 hrs. The zeolite was decanted off and another ion-exchange was repeat. The exchanged FER was filtered, washed, and dried overnight at 110° C. Right before the testing, the catalyst was calcined with air at 600° C. for 2 hrs and pressed to obtain 20/40 mesh particles. The composition of the finished catalyst had 0.12% K and <0.05% Na.

EXAMPLE 3

Preparation of FERRIERITE/$Al_2O_3$(DISPAL) Catalyst 160 g of NH4-Ferrierite from Example 2 and 40 g of an alumina binder, DISPAL (Manufactured and sold by Vista Chemical Company of Houston, Tex.), were mixed in a physical mixer. About 350 g of water was added slowly to the mixture until it became pasty. The mixture was extruded to ⅟₁₆", dried at 120° C. overnight, and calcined with air at 600° C. for 2 hrs. The catalyst was ground to 20/40 mesh for testing. The catalyst had about 20 wt % of binder.

EXAMPLE 4

Preparation of FERRIERITE/Al2O3 Catalyst

FER/$Al_2O_3$, HSZ-720KOD**, with 20% alumina binder was obtained from TOSOH. The same zeolite, HSZ-720KOA, was used in all catalysts. The catalyst was ion-exchanged, dried, calcined, and tested by the same ways as described in Example 2.

**HSZ-720 KOD—Trademark of a zeolite based ferrierite catalyst with 20% of a binder, manufactured and sold by TOYO SODA USA, Inc. of Atlanta, Ga.

EXAMPLE 5

Preparation of FERRIERITE/SiO2 and FERRIERITE/Clay Catalysts

FERRIERITE/$SiO_2$ (20%) and FERRIERITE/clay (20%) were obtained from TOSOH. The catalysts were ion-exchanged, dried, calcined, and tested by the same procedures.

EXAMPLE 6

Testing of Catalysts

The five catalysts were tested for the isomerization of 1-butene to isobutylene. Nitrogen was fed with 1-butene as a diluent The reaction conditions were: 420° C. 15.3 psia, 8.0 WHSV, 1/1 nitrogen/1-butene. All catalysts were tested in 20/40 mesh. Detailed testing procedures are described in copending Application, Ser. No. 07/990,407.

Figure 2:
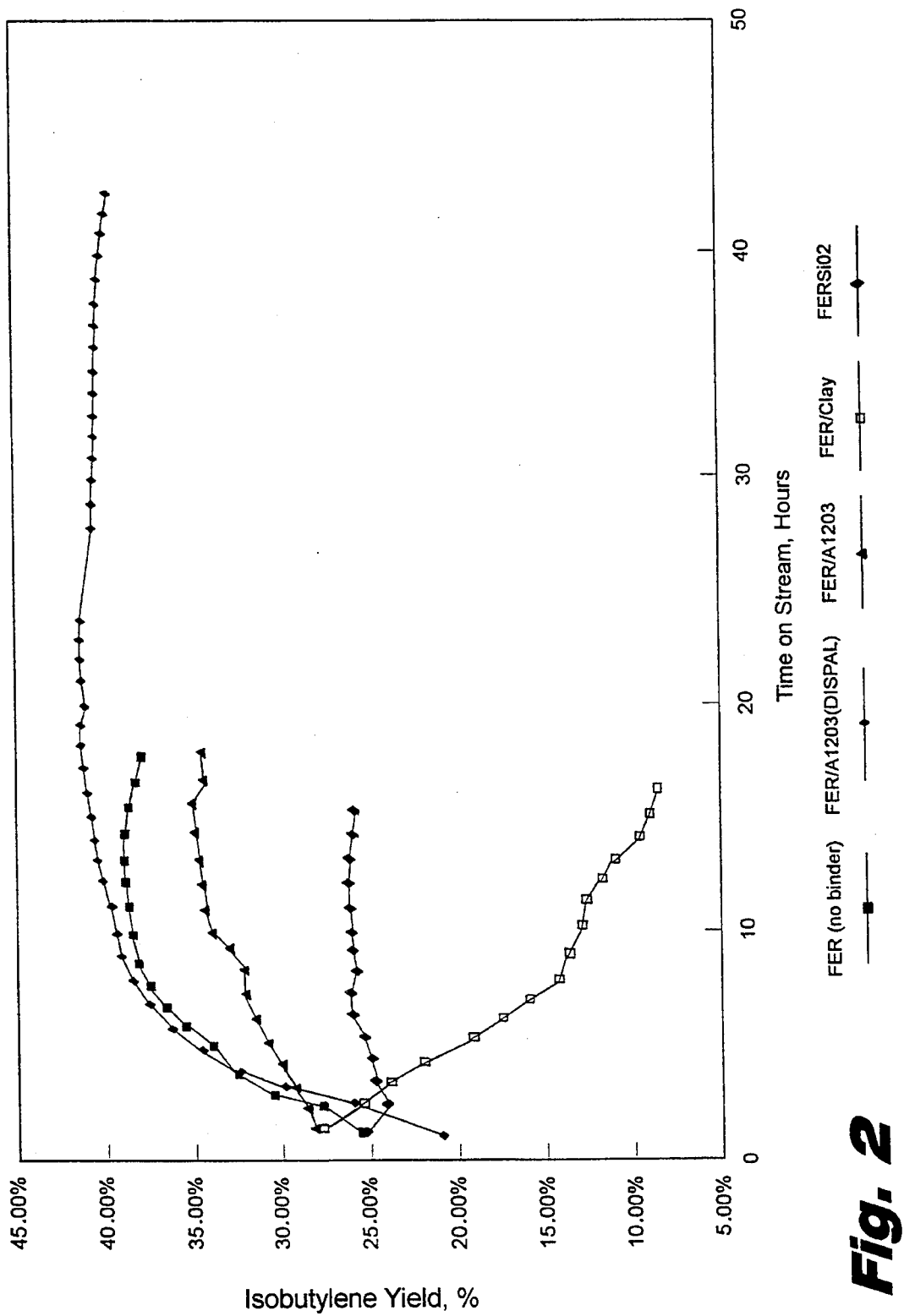
FIG. 2 is a graph of plots of isobutylene yield vs. time of ferrierite catalysts.

Table II, FIG. 1, and FIG. 2 show the results. It is clear from Table II that the DISPAL alumina bound catalyst has a better performance than that of commercial FER/$Al_2O_3$, FER/$SiO_2$, and FER/clay catalysts. Furthermore, the DISPAL alumina bound catalyst is even better than the unbound FER catalyst w.r.t the selectivity, yield, and stability. FIG. 1 shows that at the same conversion, DISPAL alumina bound catalyst has a higher yield, i.e. better selectivity. FIG. 2 shows that the DISPAL bound catalyst is more stable than the unbound catalyst. Quantitatively, the deactivation rate of DISPAL alumina bound and unbound catalysts are calculated to be 0.115 and 0.205 %/hr, respectively. The results suggest that there are synergistic interactions between DISPAL alumina binder and FER zeolite to improve the selectivity, yield, and stability.

According to the present invention, the alumina binder such as DISPAL, has a particle size of about 0.4 to about 100.0 microns.

In Table II below, DISPAL alumina is the preferred binder used according to present invention.

TABLE II

| | Effects of Binder on FER Catalysts | | | | | | |
|---|---|---|---|---|---|---|---|
| | Run Time | Average Results, % | | | Peak Results, % | | |
| Catalyst | hr | Conv. | Sel. | Yield | Conv. | Sel. | Yield |
| FER (no binder) | 17 | 51.9 | 71.7 | 35.7 | 44.9 | 86.8 | 39.0 |
| FER/Al2O3 (DISPAL) | 44 | 49.8 | 78.0 | 38.8 | 48.0 | 86.6 | 41.6 |
| FER/Al2O3 | 17 | 51.6 | 64.0 | 32.4 | 45.7 | 76.6 | 35.0 |
| FER/SiO2 | 18 | 50.6 | 52.8 | 25.7 | 45.7 | 58.1 | 26.6 |
| FER/clay | 16 | 28.2 | 59.1 | 15.8 | 57.3 | 48.2 | 27.6 |

We claim:

1. A process for the skeletal isomerization of an n-olefin of from 4 to 12 carbon atoms to provide a branched olefin product which comprises contacting the n-olefin under skeletal isomerization conditions with, as skeletal isomerization catalyst, a zeolite present in a binder, said zeolite having a pore size of at least about 4.5 angstroms and a pore structure characterized by intersecting 10-member ring and 8-member ring channels.

2. The process of claim 1 wherein the binder is selected from the group consisting of alumina, silica, silica-alumina, clay or any combination thereof.

3. The process of claim 1 wherein the skeletal isomerization conditions include a temperature of between 300° C. and 650° C., a pressure of between 0.1 and 100 atmospheres and a space velocity of n-olefin of between 0.1 and 40 weight hourly space velocity.

4. The process of claim 1 wherein the n-olefin is an n-butene.

5. The process of claim 1 wherein the zeolite is an aluminosilicate or an isomorphously substituted T-zeolite in which T is B, Ga or Fe.

6. The process of claim 1 wherein the skeletal isomerization conditions include a temperature of from 400° C. to 580° C., a pressure of from 0.5 to 4.0 atmospheres and a space velocity of n-olefin of between 1.0 and 20 weight hourly space velocity.

7. The process of claim 1 wherein the zeolite is selected from the group consisting of dachiadite, epistilbite, ferrierite, heulandite, stilbite and any combination thereof.

* * * * *